(12) United States Patent
Lin et al.

(10) Patent No.: US 8,772,003 B2
(45) Date of Patent: Jul. 8, 2014

(54) BACTERIAL CELLULOSE FILM AND USES THEREOF

(75) Inventors: Yi-Chuan Lin, Changhua County (TW); Yuh-Chyun Wey, Changhua County (TW); Mei-Ling Lee, Changhua County (TW)

(73) Assignee: Nympheas International Biomaterial Corp., Changhua County (TW)

( * ) Notice: Subject to any disclaimer, the term of this patent is extended or adjusted under 35 U.S.C. 154(b) by 231 days.

(21) Appl. No.: 13/114,014

(22) Filed: May 23, 2011

(65) Prior Publication Data

US 2011/0286948 A1 Nov. 24, 2011

(30) Foreign Application Priority Data

May 24, 2010 (TW) ................................ 99116470 A (51) Int. Cl.
*C12P 1/04* (2006.01)
*C12P 19/04* (2006.01)
(52) U.S. Cl.
CPC ..................................... *C12P 19/04* (2013.01)
USPC ......................................................... 435/170
(58) Field of Classification Search
None
See application file for complete search history.

(56) References Cited

U.S. PATENT DOCUMENTS 4,588,400 A * 5/1986 Ring et al. .................... 604/304

FOREIGN PATENT DOCUMENTS

CN 101365264 * 2/2009 ............. H04R 31/00

OTHER PUBLICATIONS

Hutchens et al., Letters in Applied Microbiology, vol. 44 (2007) pp. 175-180.*
Son et al., Biotechnol. Appl. Biochem. (2001) vol. 33, pp. 1-5.*
Chawla et al., Food Technol. Biotechnol. vol. 47 (2) pp. 107-124, 2009.*
Species: *Gluconacetobacter xylinus* (*Acetobacter xylinus*), retrieved from the Internet.*
Sun et al., Diolog translation of CN 101365264.*
European Search Report, issued Aug. 23, 2011, for counterpart application filed with EPO (EP 11 16 7341).
Tang et al., "The influence of fermentation conditions and post-treatment methods on porosity of bacterial cellulose membrane", World J. Microbiol. Biotechnol., vol. 26: 125-131 (2010).
Mendes et al., "In vivo and in vitro evaluation of an *Acetobacter xylinum* synthesized microbial cellulose membrane intended for guided tissue repair", ACTA Veterinaria Scandinavica, 51:12, 2009, pp. 1-8.
Bodin et al., "Influence of cultivation conditions on mechanical and morphological properties of bacterial cellulose tubes", Biotechnology and Bioengineering, vol. 97, No. 2, 2007, pp. 425-434.
N. N., "Hydro-Velour", Cosmoprof Asia 2009, 2009.

* cited by examiner

*Primary Examiner* — Allison Ford
*Assistant Examiner* — Yvonne Pyla
(74) *Attorney, Agent, or Firm* — Pai Patent & Trademark Law Firm; Chao-Chang David Pai (57) ABSTRACT

A bacterial cellulose film is provided, including microbial fibers consisting of bacterial cellulose, wherein the microbial fibers are arranged in a density gradient in a direction of the bacterial cellulose film thickness.

1 Claim, 7 Drawing Sheets

BACTERIAL CELLULOSE FILM AND USES THEREOF

CROSS REFERENCE TO RELATED APPLICATIONS

This application claims the priority of Taiwan patent application Ser. No. 099116470, filed May 24, 2010, and entitled "Bacterial Cellulose film and uses thereof".

The disclosure of the application is incorporated herein by reference.

BACKGROUND OF THE INVENTION

1. Field of the Invention

The present invention relates to a bacterial cellulose film, and in particular relates to a bacterial cellulose film with a density gradient in the direction of the film thickness.

2. Description of the Related Art

Bacterial cellulose (BC), also named microbial cellulose, refers to cellulose produced by microorganisms. Bacterial cellulose is formed by a linkage of β-1,4 glucosidic bonds between carbon atoms and shows properties of high purity and water content, and excellent ductility and mechanical strength. The strain for producing bacterial cellulose includes *Acetobacter xylinum*. The obtained cellulose generally forms fibers which constitute a non-woven film in a reticular structure on the surface of a culture medium. The fiber in general has a diameter of approximately 2~100 nm, which is about 1/100th fiber diameter of the plant. However, the fiber of bacterial cellulose has a chemical structure identical to the plant fiber. Because of the unique physical properties, bacterial cellulose is applicable in several fields, such as biomedical materials (EP 1,438,975, EP 0,396,344 or WO 01-61026), electronic materials (US 2008/220333), acoustics (EP 0,457, 474, U.S. Pat. No. 5,274,199 or JP 6-284495) and special papers and cosmetics (JP 10-077302, JP9-838803 or FR 2,924,342) etc.

In the field of biomedicine, the bacterial cellulose film has been considered one of the best substitutes for skin, providing effects of alleviating pain, absorbing secretions from wounds, providing wounds with water and enhancing and improving the wound recovery. The bacterial cellulose film also shows excellent biocompatibility and biosafety.

Johnson and Johnson Product Inc. has provided a dressing for burn wounds by using bacterial cellulose films with or without medicines (U.S. Pat. No. 4,588,400). WO 86/02095 discloses a method for producing a bacterial cellulose film with a thickness of about 0.2~3 mm by culturing *A. xylinum* in a medium containing Tea Sinesis as nitrogen sources and glucose as carbohydrate sources under 26~96 hours of stirring at a temperature of 28° C. A film produced by the method has been sold as a trademark BIOFILL® for treatment of skin injuries like artificial skin substitutes.

The Xylos Corporation filed several patent applications for bacterial cellulose films. For example, US 2005/0019380A1 provides a use for bacterial cellulose film to treat chronic wounds. WO2005/018435A2 and US2007/0286884A1 discloses an implantable microbial cellulose material for hard tissue repair and regeneration. EP1849463A2 provides a microbial cellulose material for use in transdermal drug delivery systems.

L'oreal Sociétié Anonyne, FR, has also filed several patent applications relating to microbial cellulose. For example, FR 2924340 discloses a use of fingers maintenance and cosmetics. FR2924342 provides a use for lip care and cosmetics. JP2009-051829 discloses a combination of microbial cellulose films and cosmetic powders. FR2916948 discloses a long-lasting perfume primarily constituted of microbial cellulose films. FR2916971 provides a microbial cellulose paste for puffy eyes.

Regarding the unique physical property, the bacterial cellulose film has been prospected for broad uses. Study for new applications and novel properties of the bacterial cellulose film are already flourishing in the field.

BRIEF SUMMARY OF THE INVENTION

A detailed description is given in the following embodiments with reference to the accompanying drawings. The cited references and publications are incorporated herein by reference.

In one aspect, the invention provides a bacterial cellulose film that comprises microbial fibers consisting of bacterial cellulose, in which the microbial fibers are arranged in a density gradient in a direction of the bacterial cellulose film thickness.

In another aspect, the invention provides a method, for producing the bacterial cellulose film, comprises a fermentation step with a low initial cell concentration in the range of $10^2$-$10^5$/ml.

In another aspect, the invention provides a method for using the bacterial cellulose film by applying the bacterial cellulose film onto a skin surface, wherein the surface of the bacterial cellulose film in contact with the skin surface has a lower density of microbial fibers than the other surface of the bacterial cellulose film.

In a further aspect, the invention provides a method for removing sebum from the skin surface by applying the bacterial cellulose film onto the skin surface, wherein the surface of the bacterial cellulose film in contact with the skin surface has a lower density of microbial fibers than the other surface of the bacterial cellulose film.

DESCRIPTION OF THE DRAWINGS

The present invention can be more fully understood by reading the subsequent detailed description and examples with references made to the accompanying drawings and attachments, wherein:

FIG. 3 shows the relative percent difference of the water loss rate for the skin surface by treatment of the bacterial cellulose film in one embodiment and a commercially available microbial cellulose sheet, in which column A refers to the relative percent difference of the water loss rate for the skin surface without being applied any material thereon (untreated skin), column B refers to the relative percent difference of the water loss rate for the skin surface treated with the upper surface of the bacterial cellulose film in a state of saturation, column C refers to the relative percent difference of the water loss rate for the skin surface treated with the lower surface of the bacterial cellulose film in a state of saturation, column D refers to the relative percent difference of the water loss rate for the skin surface treated with the upper surface of the bacterial cellulose film in a state of unsaturation, column E refers to the water loss rate of the skin surface with a treatment of a commercially available microbial cellulose sheet, and the Y-axis shows the relative percent difference of the water loss rate for the skin surface before and after treatment;

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

In one embodiment, the bacterial cellulose film consists of cellulose produced by culturing the bacteria, Gluconacetobacter xylinum, in a liquid medium. The diameter of microbial fibers for bacterial cellulose films is about 30~100 nm. After static fermentation, the microbial fibers constitute a non-woven reticular structure on the surface of the culture medium and form a semi-transparent bacterial cellulose film. In the embodiment, one bacterial cellulose film is produced at one time.

The formation of bacterial cellulose film with a density gradient of microbial fibers in a direction of the bacterial cellulose film thickness can be achieved by manipulating inoculates concentration and culture conditions. The dissolution of oxygen in the medium is critical for cell growth and biocellulose formation. Thus, the formation biocellulose films are happened at the air/liquid medium interface for static cultures. At the beginning of the cultivation, low cell concentration and/or low cell growth rate can result in loose and softer microbial fibers. Along with the culture time, the amount of bacteria increases and/or culture conditions are changed to speed up biocellulose formation. The reticular structure of biocellulose becomes tight and the density of the microbial fibers increases. In addition, bacterial cellulose films are formed at the air/liquid medium interface, the new cellulose is formed at the top of existing cellulose. The formation of bacterial cellulose film is from the top down so that each bacterial cellulose film in the medium has an upper surface contacting with the air and formed by later produced cellulose. The other surface of the bacterial cellulose film, the lower surface, is close to the bottom of the medium.

The bacterial cellulose film according to the invention has an upper surface shows a tight reticular structure and has higher density of microbial fibers. The other surface of the bacterial cellulose film, the lower surface, is close to the bottom of the medium. The lower surface consisting of earlier produced celluloses and the reticular structure is more loose and softer. As such, the lower surface has a lower density of microbial fibers than the upper surface.

Figure 1A:
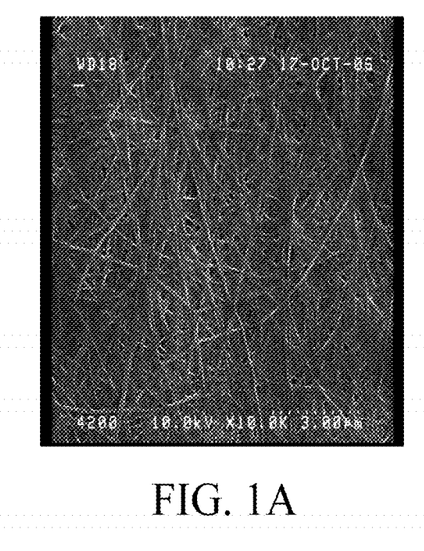
FIG. 1A shows a scanning electronic microscope (SEM) photograph showing the surface of the bacterial cellulose film in one embodiment.
Figure 1B:
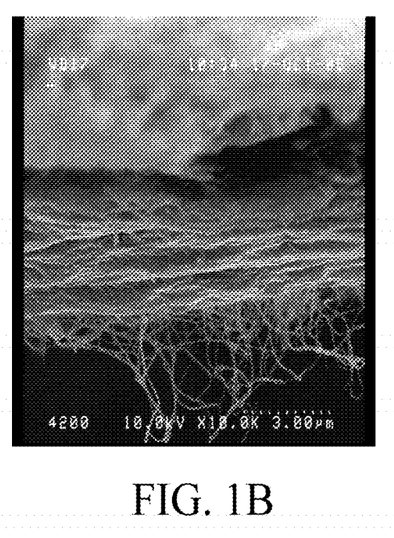
FIG. 1B is a SEM photograph showing the cross section of the bacterial cellulose film in the direction of the film thickness in one embodiment.

The difference between the upper and lower surface of the bacterial cellulose film can be observed under a scanning electron microscope (SEM). According to the cross section view in a direction of the film thickness, the upper surface shows a more dense structure while the lower surface shows several exposed microbial fibers (FIG. 1B). The difference can also be sensed by hand touch. The lower surface is smoother than the upper surface. In other words, the bacterial cellulose film shows a density gradient in the direction of the film thickness and the density decreases gradually from the upper surface to the lower surface when the film is formed in the medium.

The bacterial cellulose film of the present invention can be obtained from an incubation of microorganisms. The microorganism comprises bacteria or fungi capable of producing celluloses. More specifically, the microorganism includes Gluconacetobacter; and Gluconacetobacter xylinum is preferable. According to the present invention, the method, for producing the bacterial cellulose film, comprises a fermentation step with a low initial cell concentration in the range of $10^2$-$10^5$/ml. Specifically, a low initial cell number of Gluconacetobacter in a suitable medium at the beginning of the culture. The low number of the microorganism comprises $10^2$-$10^5$ cells/ml. In one embodiment, the medium consists of glucose, yeast extract powders, $Na_2HPO_4$ and citrate acid. However, the components of the media can be adjusted depending on the species of the cultured microorganism and the characteristics thereof following the culture techniques in the art.

The fermentation herein includes a two-step culture condition in addition to the known culture conditions, for slowing down the formation of the cellulose in the beginning of cultivation and following the high speed cellulose formation condition for a cellulose-producing microorganism. The two-step culture condition comprises a two-step culture temperature in which the first step is incubated under room temperature and the second step is incubated under a temperature higher than room temperature. More specifically, the first step is under 25~28° C. and the second step is under 29~30° C. The two-step incubation is static in one embodiment. However, the two-step culture condition may be appropriately altered depending on the desired film thickness, the water content, or the like.

In the context, the "direction of the film thickness" and "direction of the bacterial cellulose film thickness" refer to a direction that the microbial fiber accumulates to form a thickness during the production of the bacterial cellulose film. The direction of the thickness is vertical to the surface of the film.

In the context, the "density gradient" refers to a density change that gradually increases or decreases from one surface to another of the bacterial cellulose film. For example, when the bacterial cellulose film is formed in the medium and not moved, the cellulose density gradually decreases in a direction from the upper surface (away from the medium plate) to the lower surface (close to the medium plate).

Currently, large-scale production of microbial cellulose has been developed in China and South-East Asia by conventional methods. The conventional microbial cellulose is produced by artificially incubating mixed cultures in an open environment to form a bulk of cellulose. The bulk of cellulose is then sliced to obtain a cellulose sheet. Therefore, both surfaces of the cellulose sheet show identical density of the cellulose. In other words, the cellulose sheet lacks a density gradient in the direction of the thickness. Furthermore, slicing makes the cellulose sheet thicker and heavier than the film produced by culturing bacteria in sheets. As such, when in contact with human or animal skin, the cellulose sheet is unable to closely fit with the surface of skin and easily falls off because it is thick and heavy. Furthermore, microbial cellulose has a property to absorb water or solution more than 50 to 100 times that of its weight. According to the thickness, conventional biocellulose sheets need a lot of essence to rich a state of saturation which is good for active components efficiently delivered into the skin.

The bacterial cellulose film according to the invention provides a density gradient in the direction of film thickness. The surface with a lower density of the microbial fibers forms a tight fit to the surface of skin. With the saturation of water content or moisture content, water or active components contained in the film can be efficiently delivered to the skin resulting in effective transdermal delivery. In a further aspect, the invention provides a method for using the bacterial cellulose film by applying the film onto the surface of human or animal skin. Specifically, the method makes the surface of the film with a lower density of microbial fibers have contact with the surface of human or animal skin in order to obtain excellent fit for the skin and effective transdermal delivery. The term "skin" herein refers to human or animal tissues including epidermis, dermis, subcutaneous tissues, nails, hairs, glands, or the like.

Figure 6A:
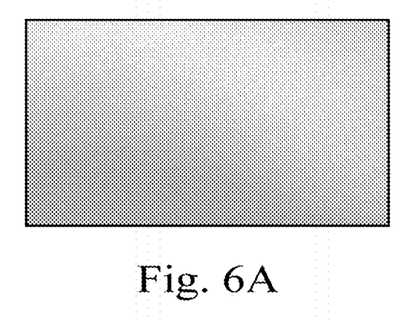
FIG. 6A shows a bacterial cellulose film in one of the embodiment before use.
Figure 6B:
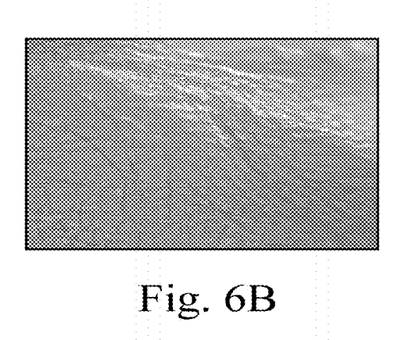
FIG. 6B shows the bacterial cellulose film of FIG. 6A after being applied to the surface of the skin, wherein the film appears the skin texture of the applied skin.

The inventors realize that the density gradient in the direction of film thickness leads the bacterial cellulose film to show excellent fitness for the skin when applying the surface with a lower density of the microbial fibers onto human or animal skin. The reason may be that the surface with a lower density of microbial fibers exposes more microbial nano-fibers and form a larger contact area with the skin. In addition, the microbial fibers contain a large number of hydroxyl groups (—OH) that easily form hydrogen bonds with the surface of human or animal skin. As such, the bacterial cellulose film is able to nicely fit the skin. In one embodiment, the bacterial cellulose film is applied onto the surface of human or animal skin for about 15 to 30 minutes. When the film was removed, the skin texture of the treated surface was clearly revealed on the film (see FIGS. 6A and 6B). In one embodiment, the bacteria cellulose film is applied on human or animal nails. In another embodiment, the bacterial cellulose film is applied on an elbow of a human arm. In this embodiment, even if the arm severely moves, the bacterial cellulose film is still closely fit onto the surface of skin. In a further embodiment, the bacterial cellulose film is applied on the face like a masque. In the embodiment, the user is free to move and the film does not fall off, decreasing the inconvenience of keeping a fixed head posture when conventionally using masques.

The dry weight of the bacterial cellulose film can be controlled by culture conditions, such as culture periods, concentration and volume of the culture medium, or the like. According to the invention, the dry weight of the bacterial cellulose film is controlled in a range of 5~20 g/m². Comparing the weight of the conventional cellulose sheet (which is more than 30 g/m²), the bacterial cellulose film is at least 33.3% lighter. Because the bacterial cellulose film is softer than conventional ones and is able to be pressed to a thickness of 0.1 mm~0.5 mm, fitness to skin is greatly elevated. The biocellulose film can be easily become saturated after soaked in water or a solution containing active components, because the film is lighter and fibers of each film are less. The saturation of water content in the bacterial cellulose film can enhance the efficiency of the transdermal delivery of water and/or active components The "saturation" in the content refers to a water content of the bacterial cellulose film that is the maxima the bacterial cellulose film can absorb under room temperature and atmospheric pressure. The water content of the bacterial cellulose film according to the invention is 90%~99% by weight based on the total weight of the film.

In one embodiment, the bacterial cellulose film absorbs water only. In another embodiment, the bacterial cellulose film contains water and other active components. The active component is not specifically limited, such as antibiotics, antimicrobials, antivirals, hemostatics, anesthetics, anti-inflammatory drugs, drugs for enhancing the healing of wounds, steroids, antihistamine, cell proliferating drugs, growth factors, proteins, nucleotides, enzymes, humectants, hyaluronic acid, ascorbic acid, kojic acid, arbutin, or the like, or a combination thereof. A person skilled in the art can follow the market demand to add appropriate amounts of the active components in the film.

Figure 7A:
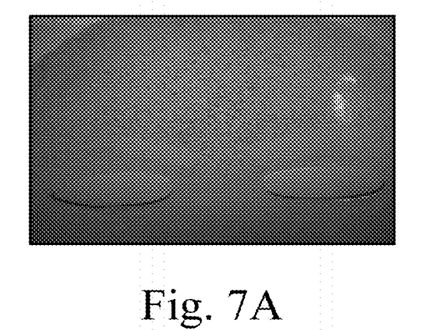
FIGS. 7A and 7B show a bacterial cellulose film in one of the embodiment after being applied to the surface of the skin, wherein the film appears the sebum of the applied skin surface.
Figure 7B:
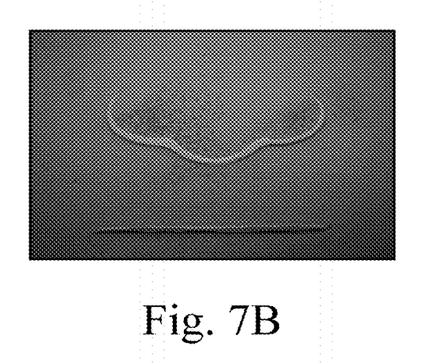

In another embodiment, the bacterial cellulose film is applied on the skin for sebum removal. Because the bacterial cellulose film nicely fits the skin, the microbial nano-fibers of the film are able to contact with the sebum in the skin pore. When the water of the film is absorbed by the skin or volatized to dry, the sebum in the skin pore is adhesive to the film due to a siphoning effect and is removed out (see FIGS. 7A and 7B). Therefore, the bacterial cellulose film of the invention is able to remove excessive sebum not only from the surface of skin but also inside skin pores. In one embodiment, the sebum amount on the skin surface is decreased 50%~100% after the bacterial cellulose film is applied for 15-60 minutes thereto compared to an untreated surface of skin.

The bacterial cellulose film of the invention is not limited in its uses and is able to be applied to any part of the surface of human or animal skin. In one embodiment, the bacterial cellulose film is applied on the surface of human or animal skin for about 15~60 minutes. In another embodiment, the film is applied on the surface of skin until the film became thin, dried or transparent and subsequently removed from the surface of the skin. In one embodiment, the film on the surface of skin is rinsed to remove. The "rinse" in the content refers to making the bacterial cellulose film moist and softened by water, lotion or solutions in order to be easily removed from the surface of the skin.

The following examples are used for describing preferred embodiments of the invention. However, the scope of the application is not limited to the examples. Any modification or improvement without departing from the spirit of the invention should be encompassed in the scope of the application.

Example 1

Figure 2:
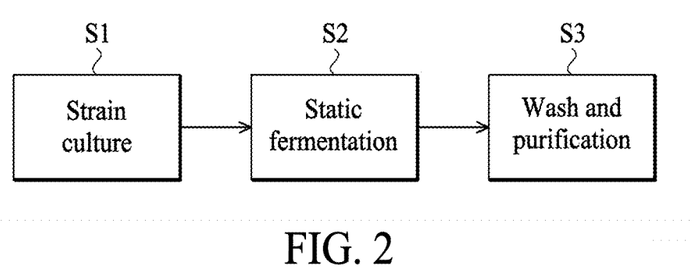
FIG. 2 is a schematic view showing the production of the bacterial cellulose film in one embodiment.

Production of the Bacterial Cellulose Film with a Density Gradient in the Direction of the Film Thickness 10~30 g/L of glucose and 5~10g/L of a yeast extract powder were used for the seed culture medium. Gluconacetobacter xylinus was implanted and cultured in this sterilized seed culture medium at 30° C. and aerated for 3~7 days (see FIG. 2, S1). A culture medium with 10~30g/L of glucose, 5~10g/L of a yeast extract powder, 2~10g/L of $Na_2HPO_4$ and 1~5g/L of citrate acid (sterilized under 121° C. for 30 minutes) were inoculated with 1~10% (v/v) seed cultures. The initial cell number should be set in the range of $10^2$-$10^5$/ml. The strain was statically fermented in A4-sized plates at 25~28° C. for 2~4 days. (see FIG. 2, S2). After that, the culture temperature was increased up to 29~32° C. for another 3~10days. Following fermentation, the bacterial cellulose film was moved out from the plate. Subsequently, the film was washed by 0.1%~5% of a NaOH aqueous solution and soaked in the solution for overnight. The film was further washed with water for 3~4 times and then neutralized with citric acid (see FIG. 2, S3). The obtained film was stored for the next steps.

Example 2

Test for Water Loss on the Surface of Skin

The bacterial cellulose film obtained from Example 1 and a commercially available cellulose sheet (ChiaMeei Food Industrial Corp., Taichung, Taiwan) were individually cut into 5 cm-diameter circles. The circular films and sheet were separately immerged in a 10% glycerol aqueous solution (glycerol was one of the humectants) and applied onto the surface of a human skin for 30 minutes, in which the film surface in contact with the skin comprised the upper surface of the bacterial cellulose film in saturation with glycerol (B), the lower surface of the bacterial cellulose film in saturation with glycerol (C), the upper surface of the bacterial cellulose film in un-saturation with glycerol (D) and the surface of the commercially available cellulose sheet (E). After that, the circular films and sheet were taken off from the skin. After 15 minutes, the treated skin surfaces were tested for water loss by a CK Electronic Multiprobe Adapter System MPA580® (Custometer) (COURAGE+KHAZAKA electronic GmbH, Germany). The untreated surface of skin (A) was tested under the same method like a control.

Figure 3:
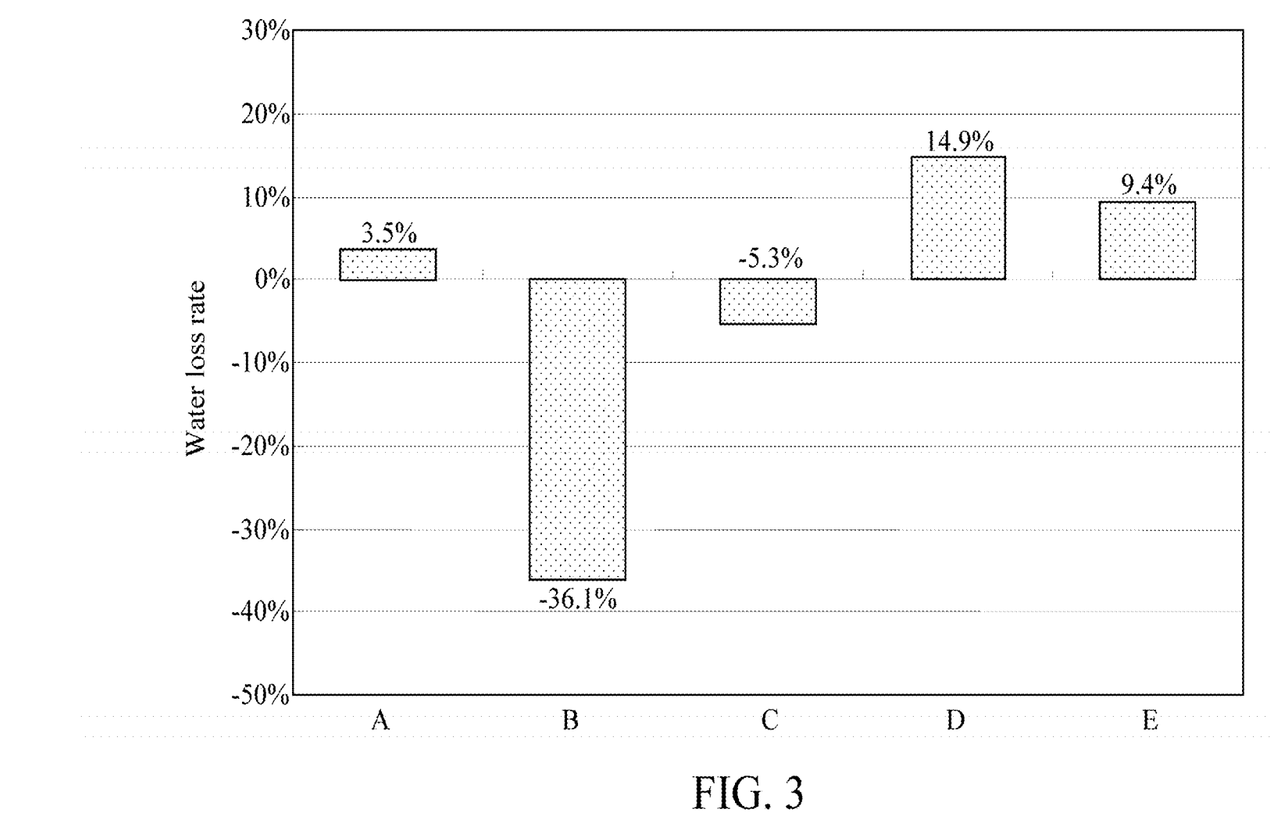

The test result is shown in FIG. 3. The water content of the skin surface before treatment was set as 0%. Compared to the 0%, the water loss decreased 36.1% after the surface of skin was applied the upper surface of the bacterial cellulose film in saturation with glycerol (B) for 30 minutes. The treatment with the lower surface of the bacterial cellulose film in saturation with glycerol (C) also showed a negative water loss rate. The result revealed that the bacterial cellulose film in a state of saturation, no mater whether the upper or lower surface was applied to the skin, was able to deliver glycerol to the skin and reduced the water loss of the skin surface. The treatment with the bacterial cellulose film in a state of unsaturation (D) and the commercially available cellulose sheet (E) showed water loss rate +14.9% and +9.4%, respectively. The result revealed that the bacterial cellulose film in a state of unsaturation and a commercially available cellulose sheet had poor effects to deliver glycerol to the skin and thus failed to effectively reduce the water loss of the skin surface.

Example 3

Test for Sebum Reduction

The bacterial cellulose film obtained from Example 1 and a commercially available cellulose sheet (ChiaMeei Food Industrial Corp., Taichung, Taiwan) were individually cut into 5 cm-diameter circles. The circular films and sheet were separately applied to a prewashed or unwashed surface of the skin of a human forehead. After about 15~40 minutes, the bacterial cellulose film was completely dried and became transparent. The commercially available cellulose sheet was still wet. The circular film and sheet were separately rinsed by water and removed from the surface of skin. After 5 minutes, the treated skin surfaces were tested for the amount of sebum secretion by a CK Electronic Multiprobe Adapter System MPA580® (Custometer) (COURAGE+KHAZAKA electronic GmbH, Germany).

Figure 4:
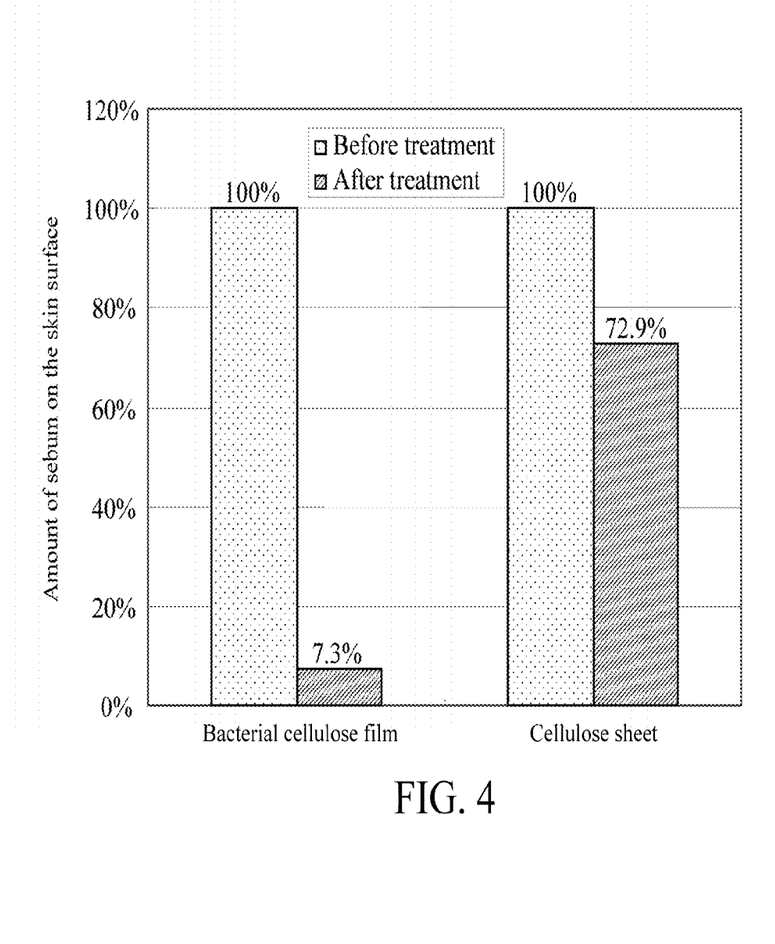
FIG. 4 shows the change of the amount of sebum on the unwashed skin surface by treatment of the bacterial cellulose film in one embodiment and a commercially available microbial cellulose sheet; and the amount of sebum on the unwashed skin surface before treatment is defined 100%.

FIG. 4 shows the test result for the circular film and sheet applied to the unwashed skin surface of the human forehead. Compared to the sebum secretion before applying the film or sheet (as 100%), the treatment of the bacterial cellulose film sheet reduced approximately 92% of the sebum from the surface of the skin, while the treatment of the commercially available sheet reduced about 30% of the sebum.

Figure 5:
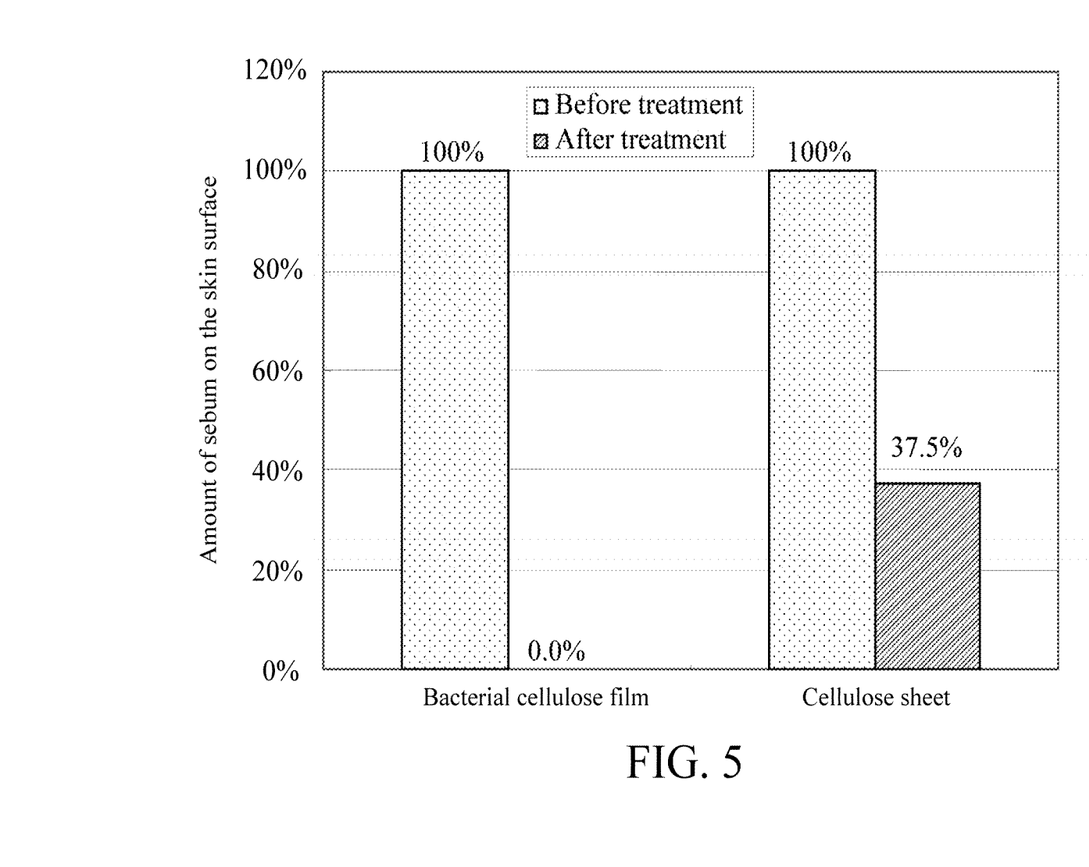
FIG. 5 shows the change of the amount of sebum on the prewashed skin surface by treatment of the bacterial cellulose film in one embodiment and the commercially available microbial cellulose sheet, and the amount of sebum on the prewashed skin surface before treatment is defined 100%.

FIG. 5 shows the test result for the circular film and sheet applied to the prewashed surface of skin of the human forehead. Compared to the sebum secretion before applying the film or sheet (as 100%), the treatment of the bacterial cellulose film reduced approximately 100% of the sebum secretion from the surface of the skin, while the treatment of the commercially available sheet reduced about 62% of the sebum.

Example 4

Test for the Water Content and Dry Weight

The bacterial cellulose film obtained from Example 1 and a commercially available cellulose sheet (ChiaMeei Food Industrial Corp., Taichung, Taiwan) were individually cut into 5 cm-diameter circles and weighted (W1). Then, the circular film and sheet were dried in an oven at 50° C. and weighted (W2). According to W1 and W2, the water content, water content per unit area, the weight of fibers per unit area and the amount of water per fiber were calculated according to the following formula. The result is shown in Table 1.

Water content=$(W1-W2) \div W2$

Water content per unit area=$[(W1-W2) \div W2] \div 25\ cm^2$

Weight of fibers per unit area $(W3) = W2 \div 25\ cm^2$

The amount of water per fiber=$(W1-W2) \div W3$

TABLE 1

The water content and dry weight of the bacterial cellulose film and commercially available sheet

| | Water content (%) | Water content per unit area (g/m²) | Weight of fibers per unit area (g/m²) | The amount of water per fiber (g/g) |
|---|---|---|---|---|
| Bacterial cellulose film in a state of saturation | 97.4 ± 0.4% | 410.6 ± 78.8 | 10.9 ± 1.3 | 37.6 ± 5.4 |
| Bacterial cellulose film in a state of unsaturation | 95.1 ± 0.8% | 232.8 ± 19.5 | 12.1 ± 2.3 | 19.8 ± 3.3 |
| Commercially available cellulose sheet | 96.7 ± 0.2% | 921.2 ± 49.0 | 31.4 ± 2.9 | 29.4 ± 1.7 |

According to Table 1, the bacterial cellulose film was clearly different when compared to the commercially available sheet in the weight of fibers per unit area. The weight of fibers per unit area for the commercially available sheet was more than 2 times than that for the bacterial cellulose film. The water content per unit area and the amount of water per fiber also showed differences between the commercially available sheet and the bacterial cellulose film. The result reveals that, the bacterial cellulose film absorbs less water to reach a state of saturation. This is the reason that the bacterial cellulose film of the invention is lighter and fit better to the skin when compared with the commercially available sheet.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method, for producing a bacterial cellulose film, comprises a static fermentation step of Gluconacetobacter, wherein the static fermentation step comprises two-step culture temperature of 25~28° C. at the first step and 29~30° C. at the second and starts from initial concentration of Gluconacetobacter in a range of $10^2$-$10^5$/ml, and wherein the bacterial cellulose film comprises microbial fibers consisting of bacterial cellulose and the microbial fibers are arranged in a density gradient in a direction of the bacterial cellulose film thickness.

* * * * *